(12) United States Patent
Shimizu et al.

(10) Patent No.: US 6,235,865 B1
(45) Date of Patent: May 22, 2001

(54) PHOSPHONIUM BORATE COMPOUND, MAKING METHOD, CURING CATALYST, AND EPOXY RESIN COMPOSITION

(75) Inventors: Hisashi Shimizu, Selangor (MY); Minoru Takei; Toshio Shiobara, both of Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/345,390

(22) Filed: Jun. 30, 1999

(30) Foreign Application Priority Data

Jul. 2, 1998 (JP) .................................................. 10-202742

(51) Int. Cl.[7] .............................. B01J 31/22; C07F 9/54; C08K 5/50; C08L 63/00
(52) U.S. Cl. ........................... 528/89; 502/164; 523/445; 568/2
(58) Field of Search .............................. 528/89; 523/451, 523/445; 502/164; 568/2

(56) References Cited

U.S. PATENT DOCUMENTS

| Re. 32,951 | * | 6/1989 | Whiteside, Jr. et al. | 528/89 |
| 4,382,130 | * | 5/1983 | Ellison et al. | 528/89 X |
| 4,422,975 | * | 12/1983 | Mitchell | 568/2 X |
| 5,055,619 | * | 10/1991 | Gitzel et al. | 568/2 |

FOREIGN PATENT DOCUMENTS

| 2527116 | * | 1/1976 | (DE) | 528/89 |
| 3938200 | * | 5/1991 | (DE) | 528/89 |
| B2 56-45491 | | 10/1981 | (JP). | |
| A9 328535 | | 12/1997 | (JP). | |

* cited by examiner

Primary Examiner—Richard D. Lovering

(57) ABSTRACT

Phosphonium borate compounds of formula (1) are novel.

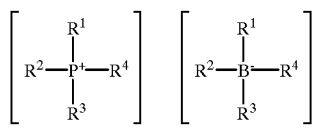

(1)

$R^1$, $R^2$, $R^3$ and $R^4$ each are a monovalent organic group having an aromatic or heterocyclic ring or a monovalent aliphatic group, at least one of $R^1$, $R^2$, $R^3$ and $R^4$ which are bonded to phosphorus atom and at least one of $R^1$, $R^2$, $R^3$ and $R^4$ which are bonded to boron atom are each an organic group derived by releasing a proton from a proton donor selected from among an aromatic carboxylic acid having at least one carboxyl group, an aromatic carboxylic acid having at least one acid anhydride group and at least one carboxyl group, a phenol compound having at least one phenolic hydroxyl group, an aromatic compound having at least one carboxyl group and at least one phenolic hydroxyl group, and an aliphatic carboxylic acid having at least one carboxyl group. The phosphonium borate compounds are useful as a latent curing catalyst for epoxy resin compositions. The epoxy resin compositions are improved in shelf stability, fast-curing ability and flow and cure into products having moisture resistance and improved electrical properties.

13 Claims, 1 Drawing Sheet

PHOSPHONIUM BORATE COMPOUND, MAKING METHOD, CURING CATALYST, AND EPOXY RESIN COMPOSITION

This invention relates to novel phosphonium borate compounds useful as a curing catalyst in epoxy and other resin compositions, and a method for preparing the same. It also relates to a curing catalyst and an epoxy resin composition comprising the same.

BACKGROUND OF THE INVENTION

The current mainstream in the semiconductor industry resides in diodes, transistors, ICs, LSIs and VLSIs of the resin encapsulation type. Epoxy resin compositions comprising an epoxy resin, curing agent and additives have superior moldability, adhesion, electrical properties, mechanical properties, and moisture resistance to other thermosetting resins. It is thus a common practice to encapsulate semiconductor devices with epoxy resin compositions. Recently, the semiconductor devices are increasing their degree of integration and accordingly becomes larger in chip size. By contrast, the outer configuration of packages is reduced in size or thickness in order to meet the demand for size and weight reduction of electronic equipment. As to the method of mounting semiconductor parts on circuit boards, the surface mounting of semiconductor parts becomes predominant since the parts on boards are increased in density.

For the surface mounting of semiconductor devices, a method of dipping entire semiconductor devices in a solder bath and a method of passing them through a hot zone where solder is melted are commonly employed. These methods bring about thermal shocks, by which the encapsulating resin layer can be cracked or separation occur at the interface between the lead frame or chip and the encapsulating resin. Such cracks or separation becomes more outstanding if the encapsulating resin layer on semiconductor devices has picked up moisture prior to the thermal shocks during surface mounting. In actual working processes, it is impossible to avoid the moisture absorption of the encapsulating resin layer. As a consequence, the semiconductor devices encapsulated with epoxy resins often suffer from a serious loss of reliability after surface mounting. One common countermeasure against such a popcorn phenomenon is to load epoxy resins with large amounts of filler for reducing moisture absorption. Also one approach for improving the molding of thin packages is to reduce the viscosity of epoxy resin compositions. Further, fast curing catalysts have also been studied to shorten the molding cycle for increasing productivity.

Prior art curing catalysts, for example, imidazole derivatives, tertiary amine compounds, tertiary phosphine compounds and derivatives thereof are less stable during shelf storage. When resins are milled therewith, these curing catalysts give rise to such problems as an increased viscosity upon milling and poor flow upon molding.

JP-B 56-45491 discloses an epoxy resin composition comprising an epoxy resin and a curing agent. The curing agent is obtained by heat treating a mixture of a novolac type phenolic resin and tetraphenylphosphonium tetraphenylborate (abbreviated as TPP-K, hereinafter) at a temperature above the softening point of the novolac type phenolic resin until the resin system is colored to be yellowish brown or brown. Allegedly this epoxy resin composition is shelf stable and produces cured products having improved moisture resistance. However, because of a low activity and poor fast-curing ability, this curing catalyst must be used in large amounts, rather detracting from the shelf stability of the epoxy resin composition.

TPP-K itself is a useful curing catalyst. Although it has good latency in that reaction starts above a certain temperature, it lacks fast-curing ability. JP-A 9-328535 discloses a thermosetting resin composition using as a catalyst a modified compound of TPP-K with only the boron atom being substituted. However, this modified compound of TPP-K with only the boron atom being substituted has a catalytic activity which cannot fully comply with the recent demand for fast curing. Thus phosphorus catalysts having higher activity are desired. Triphenylphosphine which is generally used from the past has a superior fast-curing ability, but is poor in shelf stability.

The prior art curing catalysts are thus difficult to produce epoxy resin compositions which are improved in shelf stability and flow and have excellent properties including fast curing, latency and moisture resistance.

SUMMARY OF THE INVENTION

An object of the present invention is to provide a novel and improved phosphonium borate compound, a method for preparing the same, a curing catalyst comprising the same, and an epoxy resin composition, the phosphonium borate compound being improved in that when it is blended in an epoxy resin composition, the composition has good flow, fast-curing ability and latency and cures into a product having improved moisture resistance etc.

Making efforts to solve the above-mentioned problems of an epoxy resin composition comprising an epoxy resin, a phenolic resin curing agent, and an inorganic filler, we have found that a phosphonium borate salt of the following general formula (1) is obtained by reacting a phosphonium borate compound of the following general formula (2) with one or more compounds of the following general formula (3) at a temperature of 120 to 250° C. The phosphonium borate salt of formula (1) is an effective curing catalyst for the epoxy resin and phenolic resin curing agent. The phosphonium borate salt of formula (1) is a good latent catalyst in that reaction starts above a certain temperature, as compared with the prior art triphenyl phosphine catalyst, and has high activity and reactivity as compared with TPP-K. Additionally, this salt is fully compatible with resins. Accordingly, an epoxy resin composition having the phosphonium borate salt of formula (1) blended as a curing catalyst has good flow, fast-curing ability, latency and shelf stability and cures into a product having improved moisture resistance.

In a first aspect, the invention provides a phosphonium borate compound of the following general formula (1):

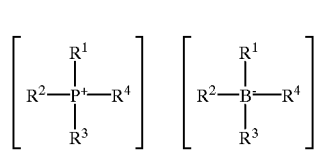

(1)

wherein $R^1$, $R^2$, $R^3$ and $R^4$, which may be the same or different, each are a monovalent organic group having an aromatic or heterocyclic ring or a monovalent aliphatic group, at least one of $R^1$, $R^2$, $R^3$ and $R^4$ which are bonded to phosphorus atom and at least one of $R^1$, $R^2$, $R^3$ and $R^4$ which are bonded to boron atom are each an organic group derived by releasing a proton from a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule.

In a second aspect, the invention provides a method for preparing a phosphonium borate compound of formula (1), comprising the step of reacting at a temperature of 120 to 250° C. a phosphonium borate compound of the following general formula (2) with at least one compound of the following general formula (3):

wherein $R^5$ is a monovalent organic group having an aromatic ring, and $R^6$ is a monovalent organic group having an aromatic or heterocyclic ring or a monovalent aliphatic group. The compound of formula (3) is a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule.

In a third aspect, the invention provides a curing catalyst for epoxy resin compositions comprising the phosphonium borate compound.

An epoxy resin composition comprising the curing catalyst is also contemplated herein.

BRIEF DESCRIPTION OF THE DRAWING

The only figure.

DESCRIPTION OF THE PREFERRED EMBODIMENTS

Figure 1:
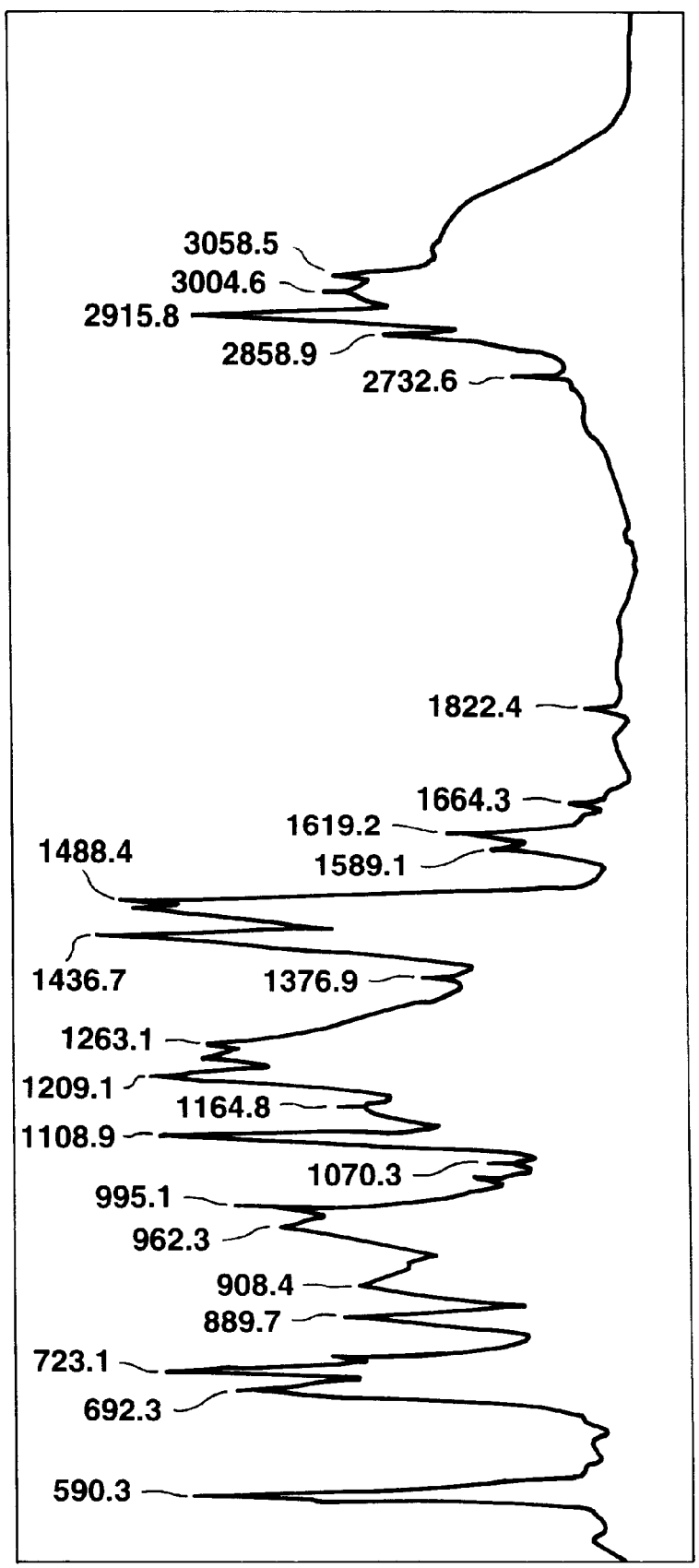
FIG. 1 is an IR absorption spectrum of Reaction Product B in Example 2.

The novel phosphonium borate compound of the invention is represented by the following general formula (1).

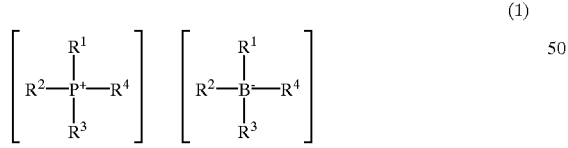

Herein $R^1$, $R^2$, $R^3$ and $R^4$ each are a monovalent organic group having an aromatic or heterocyclic ring or a monovalent aliphatic group. At least one of $R^1$, $R^2$, $R^3$ and $R^4$ which are bonded to phosphorus atom and at least one of $R^1$, $R^2$, $R^3$ and R which are bonded to boron atom are each an organic group derived by releasing a proton from a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule. $R^1$, $R^2$, $R^3$ and $R^4$ may be the same or different.

The organic group derived by releasing a proton from a proton donor is exemplified by groups of the following formulae (5) to (13).

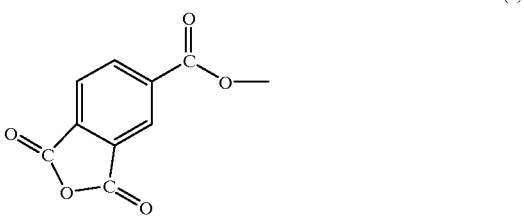

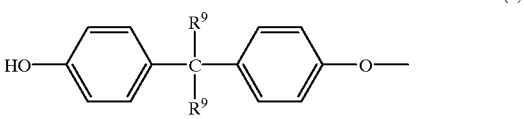

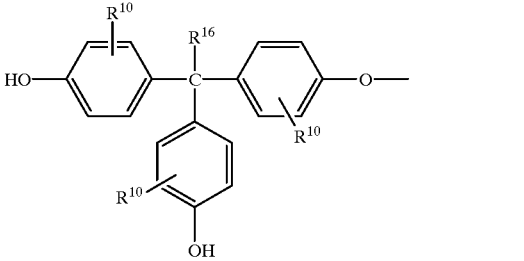

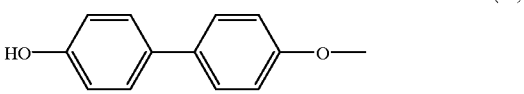

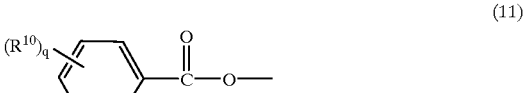

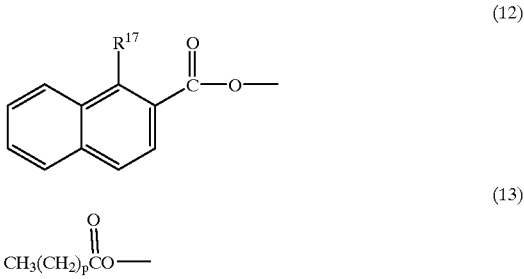

Herein $R^8$ is a halogen atom, alkoxy group or substituted or unsubstituted monovalent hydrocarbon group, $R^9$ is hydrogen, methyl or $CF_3$ group, $R^{10}$ is hydrogen or a substituted or unsubstituted monovalent hydrocarbon group, $R^{16}$ is hydrogen, methyl or ethyl, preferably hydrogen, $R^{17}$ is hydrogen or hydroxyl, p is an integer of 10 to 40, especially 11 to 31, and q is an integer of 1 to 3, especially 1 or 2.

Among the substituents represented by $R^8$, the halogen atoms include fluorine, chlorine, bromine and iodine; and the alkoxy groups include those of about 1 to 4 carbon atoms, such as methoxy, ethoxy, propoxy, isopropoxy, butoxy, and tert-butoxy. The substituted or unsubstituted monovalent hydrocarbon groups represented by $R^8$ and $R^{10}$ are preferably those of 1 to 10 carbon atoms, especially 1 to 8 carbon atoms, for example, alkyl groups such as methyl, ethyl, propyl, isopropyl, butyl, isobutyl, tert-butyl, pentyl, hexyl, cyclohexyl, and octyl; alkenyl groups such as vinyl, allyl, propenyl, isopropenyl, butenyl, isobutenyl, and hexenyl; aryl groups such as phenyl, tolyl and xylyl; aralkyl groups such as benzyl, phenylethyl, and phenylpropyl; and substituted monovalent hydrocarbon groups in which some or all of the hydrogen atoms on the foregoing groups are replaced by halogen atoms, for example, halo-substituted alkyl groups such as chloromethyl, bromoethyl, and 3,3,3-trifluoropropyl. Of these, monovalent hydrocarbon groups free of an aliphatic unsaturated bond are preferable.

Examples of the group of formula (6) are given below.

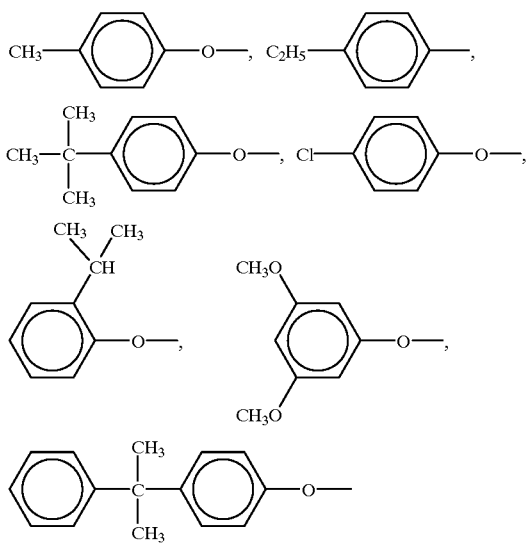

Examples of the group of formula (13) are given below.

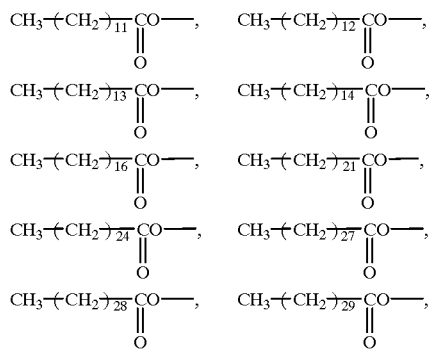

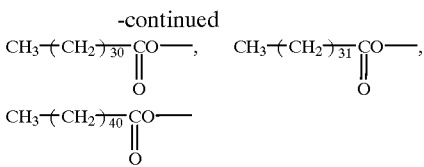

Besides the organic groups derived by releasing a proton from a proton donor, $R^1$, $R^2$, $R^3$ and $R^4$ represent substituted or unsubstituted aromatic hydrocarbon groups, for example, phenyl groups and substituted phenyl groups in which one to five hydrogen atoms, especially one or two hydrogen atoms are replaced by alkyl groups of 1 to 4 carbon atoms, especially 1 to 2 carbon atoms, alkoxy groups of 1 to 4 carbon atoms, especially 1 to 2 carbon atoms, or halogen atoms.

Typical of the phosphonium borate compounds of formula (1) are compounds of the following general formula (4):

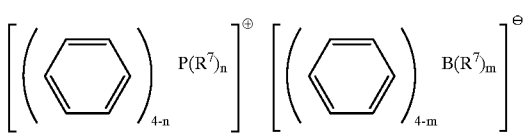

wherein n and m each are an integer of 1 to 4, and $R^7$ is a group selected from formulae (5) to (13).

The phosphonium borate compound of formula (1) can be prepared by reacting a phosphonium borate compound of the following general formula (2) with at least one compound of the following general formula (3) at a temperature of 120 to 250° C.

Herein $R^5$ is a monovalent organic group having an aromatic ring, and $R^6$ is a monovalent organic group having an aromatic or heterocyclic ring or a monovalent aliphatic group. The compound of formula (3) is a proton donor selected from among an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule.

More illustratively, $R^5$ represents substituted or unsubstituted aromatic hydrocarbon groups, for example, phenyl groups and substituted phenyl groups in which one to five hydrogen atoms, especially one or two hydrogen atoms are replaced by alkyl groups of 1 to 4 carbon atoms, especially 1 to 2 carbon atoms, alkoxy groups of 1 to 4 carbon atoms, especially 1 to 2 carbon atoms, or halogen atoms.

The compound of formula (3) or $R^6$ is exemplified by compounds of the following formulae (15) to (23).

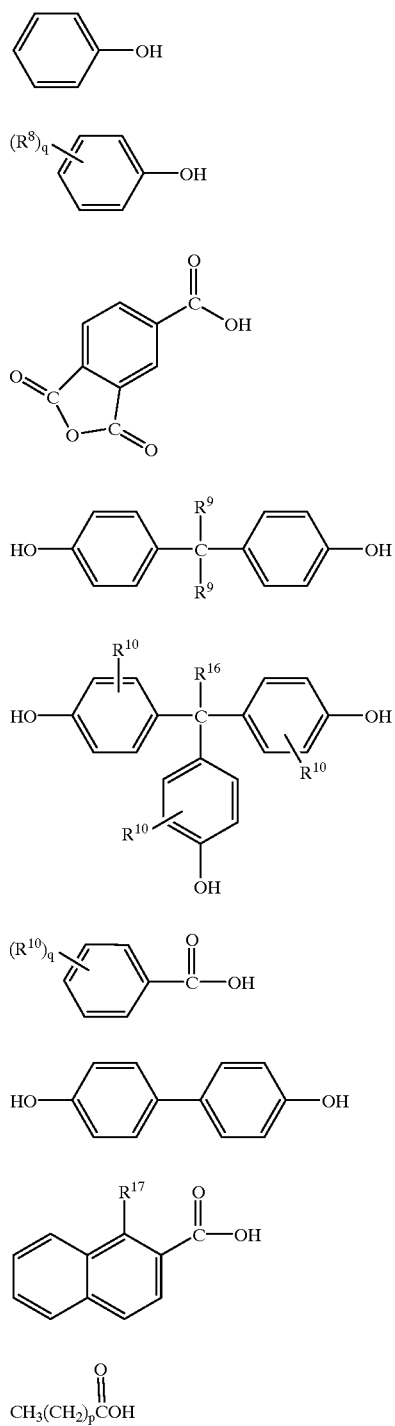

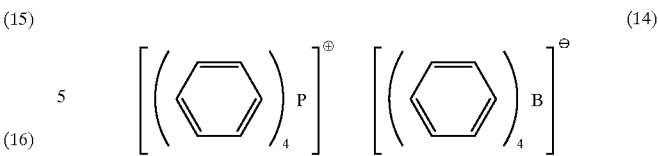

In these formulae, $R^8$, $R^9$, $R^{10}$, $R^{16}$, $R^{17}$, p and q are as defined above.

The phosphonium borate compound of formula (4) can be prepared by reacting a phosphonium borate compound of the following formula (14) with at least one of compounds of the above formulae (15) to (23) at a temperature of 120 to 250° C.

In the substitution reaction using the proton donative compounds, both the phosphorus atom and boron atom undergo substitution reaction. As to the rate of substitution reaction, the substitution reaction on boron atom is generally faster than the substitution reaction on phosphorus atom. However, since these substitution reactions are affected by the identity of the substituents originally attached to the phosphorus and boron atoms and the substituent(s) on the proton donative compound, the boron atom is not always subject to preferential substitution reaction.

The substituted phosphonium borate compound to be blended in an epoxy resin composition has a catalytic activity which varies with the proportion of substitution. That is, the greater the proportion of substitution, the higher become the catalytic activity and latency of the catalyst. Inversely, with less substituents, the catalyst has a relatively low catalytic activity and latency. As the degree of substitution reaction increases, the reacted phosphonium borate compound tends to lower its melting point and become more soluble in solvents such as acetone, chloroform, tetrahydrofuran, methyl ethyl ketone and methyl isobutyl ketone. These multi-substituted phosphonium borate compounds are highly compatible with (or soluble in) epoxy resin compositions and exert higher catalytic activity.

In the method of the invention, high-boiling solvents such as dimethyl sulfoxide and dimethylformamide are used as the reaction solvent because of the need to control the reaction temperature within the range of 120 to 250° C. although the reaction may be carried out in a solventless system.

The reaction temperature is in the range of 120 to 250° C., preferably 180 to 220° C. Temperatures below 120° C. are insufficient to drive the reaction whereas the reaction product can be decomposed above 250° C. If oxygen is present in the reaction system, oxidative decomposition reaction of the phosphonium borate compound can take place. For this reason, it is desired that oxygen be fully removed from the reaction system and that reaction be carried out in an inert atmosphere such as nitrogen. The time for substitution reaction to take place is usually about 30 minutes to about 8 hours. When the solvent is used, the solvent is removed from the reaction mixture. The reaction product is extracted with a suitable solvent such as chloroform or acetone and dried, obtaining the end substituted phosphonium borate compound. When the product is obtained as a mixture of compounds having different numbers of substituents, the respective compounds can be isolated by column fractionation although the mixture of compounds having different numbers of substituents may be used as such.

The phosphonium borate compound of the invention can be used as a curing catalyst in epoxy resin compositions or the like. When the phosphonium borate compound of the invention is used as a curing catalyst in epoxy resin compositions, the reaction product is finely divided before use or dispersed in a phenolic resin before use. The amount of the curing catalyst used is preferably 0.1 to 15 parts, more preferably 0.3 to 7 parts by weight per 100 parts by weight of the resin components combined (i.e., the total amount of the epoxy resin and the phenolic resin curing agent). Less than 0.1 part of the curing catalyst would fail to achieve brief curing. More than 15 parts of the curing catalyst would provide a too high curing rate to form a satisfactory molded part, adversely affect shelf stability, and result in a cured part containing a larger amount of water-extractable chlorine and having poor electrical properties.

The epoxy resin composition of the invention contains the above-described phsphonium borate compound as a curing catalyst in addition to an epoxy resin and a curing agent as essential components.

The epoxy resin composition is described in detail. The epoxy resin used herein is not critical insofar as it has at least two epoxy groups in one molecule. Exemplary are bisphenol type epoxy resins such as bisphenol A type epoxy resins and bisphenol F type epoxy resins, novolac type epoxy resins such as phenol novolac type epoxy resins and cresol novolac type epoxy resins, alicyclic epoxy resins, glycidyl type epoxy resins, biphenyl type epoxy resins, naphthalene ring-bearing epoxy resins, aralkyl type epoxy resins such as phenol aralkyl type epoxy resins and biphenyl aralkyl type epoxy resins, cyclopentadiene-bearing epoxy resins, and polyfunctional epoxy resins such as triphenol alkane type epoxy resins. A suitable mixture of these epoxy resins is also acceptable. For high loading of inorganic filler, biphenyl type epoxy resins and naphthalene ring-bearing epoxy resins are desirable. Those epoxy resins having a softening point of 50 to 100° C. and an epoxy equivalent of 100 to 400 are desirable. Brominated epoxy resins may also be used if flame retardance is needed.

Useful curing agents are phenolic resins. Exemplary phenolic resins are those having at least two phenolic hydroxyl groups including novolac type phenolic resins such as phenol novolac resins and cresol novolac resins, triphenolalkane type resins such as triphenolmethane resins and triphenolpropane resins, aralkyl type phenolic resins such as phenol aralkyl resins and biphenyl aralkyl resins, naphthalene ring-bearing phenolic resins, cyclopentadiene-bearing phenolic resins, and terpene ring-bearing phenolic resins. Of these, those phenolic resins having a softening point of 60 to 120° C. and/or a phenolic hydroxyl equivalent of 90 to 150 are preferable. The phenolic resin may be used in any desired amount as long as the equivalent ratio (mol/mol) of phenolic hydroxyl groups in the phenolic resins to epoxy groups in the epoxy resins ranges from 0.5:1 to 2.0:1. Often 30 to 100 parts, preferably 40 to 70 parts by weight of the phenolic resin is used per 100 parts by weight of the epoxy resin. Less than 30 parts of the phenolic resin would fail to provide strength whereas above 100 parts, some of the phenolic resin is left unreacted, detracting from moisture resistance.

An inorganic filler is preferably blended in the epoxy resin composition of the invention serving as an encapsulant for semiconductor devices. The inorganic filler is blended to reduce the expansion coefficient of the composition for reducing the stress applied to semiconductor devices. Typical inorganic fillers are fused silica in ground (fragmental) or spherical shape and crystalline silica while alumina, silicon nitride, aluminum nitride, etc. are also useful as the filler. The inorganic filler preferably has a mean particle size of about 5 to 40 $\mu$m, especially 10 to 30 $\mu$m. The mean particle size may be determined as the weight average value (median diameter) using a particle size distribution measurement apparatus based on the laser light diffraction technique. The inorganic filler of this type is preferably surface treated with silane coupling agents prior to use. Preferably about 200 to 1,000 parts by weight, especially 250 to 900 parts by weight of the inorganic filler is blended per 100 parts by weight of the resin components combined (i.e., the total amount of the epoxy resin and the phenolic resin curing agent). On this basis, a composition loaded with less than 200 parts of the filler would have a higher coefficient of expansion, with a risk of greater stresses being applied to semiconductor devices and thus deteriorating the characteristics thereof. A composition loaded with more than 1,000 parts of the filler would have an increased viscosity and thus become difficult to mold.

In the epoxy resin composition, a flexibility imparting agent based on silicone is preferably added for stress reduction. Exemplary flexibility imparting agents are silicone rubber powder, silicone gel, and block polymers of an organic resin and a silicone polymer. Instead of adding the flexibility imparting agent, the inorganic filler may be surface treated with two-part type silicone rubber or silicone gel. The flexibility imparting agent is preferably used in an amount of up to 10% (i.e., 0 to 10%), more preferably 0.5 to 10%, especially 1 to 5% by weight based on the entire composition. Less than 0.5% of the flexibility imparting agent would fail to provide satisfactory impact resistance whereas more than 10% would adversely affect mechanical strength.

In the epoxy resin composition of the invention, the novel phosphonium borate compound of the first aspect of the invention is blended as a curing catalyst as described above while if necessary, another catalyst may be additionally used. Such catalysts include imidazole and derivatives, phosphine derivatives such as triphenylphosphine, tris-p-methoxyphenylphosphine, and tricyclohexylphosphine, and cycloamidine derivatives such as 1,8-dizabicyclo(5.4.0) undecene-7.

Other optional components may be added to the epoxy resin composition insofar as the objects of the invention are not impaired. These optional components include mold release agents such as carnauba wax, higher fatty acids, and synthetic waxes, thermoplastic resins such as MBS resins, silane coupling agents, antimony oxide, and phosphorus compounds.

The epoxy resin composition of the invention is prepared by uniformly agitating and mixing predetermined amounts of the above-described components, and milling the mixture in a kneader, roll mill or extruder preheated at 70 to 95° C. The mixture is then cooled and comminuted, yielding a molding material. The order of mixing the components is not critical.

The thus obtained epoxy resin composition of the invention is effectively used in the encapsulation of various semiconductor devices, such as ICs, LSIs, transistors, thyristors, and diodes as well as the manufacture of printed circuit boards. In encapsulating semiconductor devices, the epoxy resin composition is desirably molded at about 150 to 180° C. and post cured at about 150 to 180° C. for about 2 to 16 hours.

There has been described a phosphonium borate compound which is useful as a curing catalyst in an epoxy resin composition. The epoxy resin composition having the phosphonium borate compound blended therein is improved in shelf stability, latency, fast curing and flow and cures into a product having moisture resistance and improved electrical properties.

EXAMPLE

Examples of the invention are given below by way of illustration and not by way of limitation. All parts are by weight.

Example 1

A 1-liter four-necked flask equipped with a thermometer, stirrer, and reflux condenser was charged with 16.3 parts (0.025 mol) of TPP-K, that is tetraphenylphosphonium tetraphenylborate, 40.0 parts (0.425 mol) of phenol, and 250 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the unreacted phenol and the dimethyl sulfoxide reaction solvent were distilled off in vacuum (2 mmHg) at 100° C. Extraction with chloroform yielded 16.5 g of a mixture of phosphonium borate compounds of the following formula (designated Reaction Product A, number average molecular weight 722).

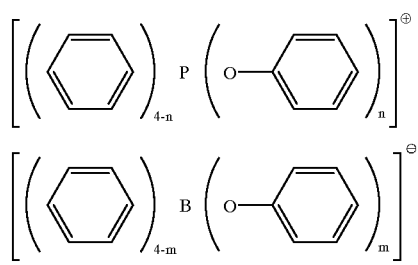

In the formula, n and m are integers of 1 to 4.

Example 2

A 1-liter four-necked flask equipped with a thermometer, stirrer, and reflux condenser was charged with 16.3 parts (0.025 mol) of TPP-K, 45.9 parts (0.425 mol) of p-cresol, and 250 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the unreacted p-cresol and the dimethyl sulfoxide reaction solvent were distilled off in vacuum (2 mmHg) at 100° C. Extraction with chloroform yielded 17.2 g of a mixture of phosphonium borate compounds of the following formula (designated Reaction Product B, number average molecular weight 778).

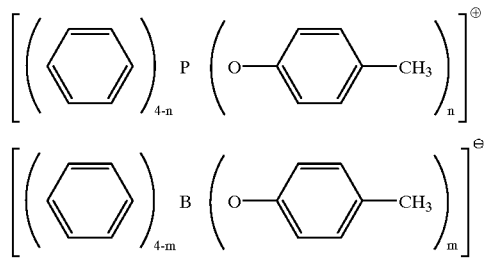

In the formula, n and m are integers of 1 to 4.

The compound thus obtained was examined by elemental analysis, with the results shown below. On analysis by NMR and IR absorption spectroscopy, it was confirmed to be a compound of the above formula. It was confirmed by liquid chromatography that n and m are integers of 1 to 4. The IR absorption spectrum of this compound is shown in FIG. 1.

| Elemental analysis | C | H | P | B |
|---|---|---|---|---|
| Calcd. (m + n = 4, %) | 80.2 | 6.17 | 3.98 | 1.38 |
| Found | 79.8 | 6.81 | 4.21 | 1.23 |

Example 3

A 1-liter four-necked flask equipped with a thermometer, stirrer, and reflux condenser was charged with 16.3 parts (0.025 mol) of TPP-K, 81.6 parts (0.425 mol) of trimellitic anhydride, and 450 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the unreacted trimellitic anhydride and the dimethyl sulfoxide reaction solvent were distilled off in vacuum (2 mmHg) at 180° C. Extraction with chloroform yielded 25.4 g of a mixture of phosphonium borate compounds of the following formula (designated Reaction Product C, number average molecular weight 1,114).

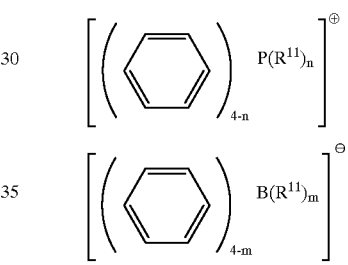

In the formula, n and m are integers of 1 to 4, and $R^{11}$ is represented by the following formula.

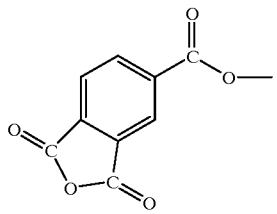

A 1-liter four-necked flask equipped with a thermometer, stirrer, and reflux condenser was charged with 16.3 parts (0.025 mol) of TPP-K, 45.6 parts (0.2 mol) of 2,2'-bis(4-hydroxyphenyl)propane, and 450 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the dimethyl sulfoxide reaction solvent was distilled of f in vacuum (2 mmHg) at 180° C. Extraction with chloroform yielded 57.7 g of a mixture of phosphonium borate compounds of the following formula (designated Reaction Product D, number average molecular weight 1,259).

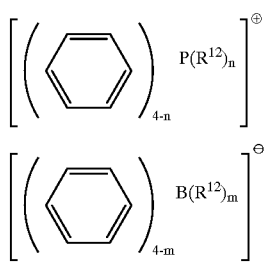

In the formula, n and m are integers of 1 to 4, and $R^{12}$ is represented by the following formula.

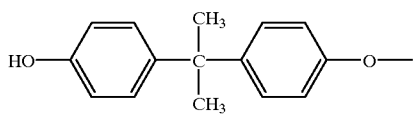

Example 5

A 1-liter four-necked flask equipped with a thermometer, stirrer, and reflux condenser was charged with 16.3 parts (0.025 mol) of TPP-K, 58.4 parts (0.2 mol) of triphenolmethane, and 450 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the dimethyl sulfoxide reaction solvent was distilled off in vacuum (2 mmHg) at 180° C. Extraction with chloroform yielded 68.7 g of a mixture of phosphonium borate compounds of the following formula (designated Reaction Product E, number average molecular weight 1,514).

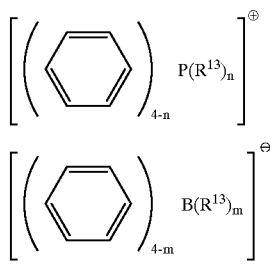

In the formula, n and m are integers of 1 to 4, and $R^{13}$ is represented by the following formula.

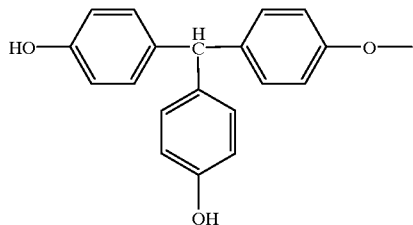

Example 6

A 1-liter four-necked flask equipped with a thermometer, stirrer, and reflux condenser was charged with 16.3 parts (0.025 mol) of TPP-K, 27.6 parts (0.2 mol) of salicylic acid, and 450 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the dimethyl sulfoxide reaction solvent was distilled off in vacuum (2 mmHg) at 180° C. Extraction with chloroform yielded 42.6 g of a mixture of phosphonium borate compounds of the following formula (designated Reaction Product F, number average molecular weight 898).

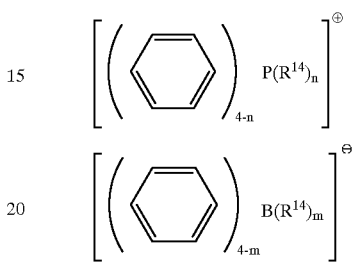

In the formula, n and m are integers of 1 to 4, and $R^{14}$ is represented by the following formula.

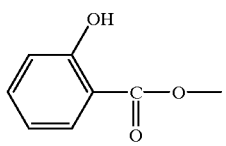

Example 7

A 1-liter four-necked flask equipped with a thermometer, stirrer, and reflux condenser was charged with 16.3 parts (0.025 mol) of TPP-K, 34.4 parts (0.2 mol) of 1-naphthenic acid, and 450 ml of dimethyl sulfoxide. With stirring in a nitrogen atmosphere, the mixture was heated to the boiling point of dimethyl sulfoxide which was equal to 182° C., at which temperature reaction was effected for 5 hours. From the reaction solution, the unreacted 1-naphthenic acid and the dimethyl sulfoxide reaction solvent were distilled off in vacuum (2 mmHg) at 180° C. Extraction with chloroform yielded 48.5 g of a mixture of phosphonium borate compounds of the following formula (designated Reaction Product G, number average molecular weight 1,034).

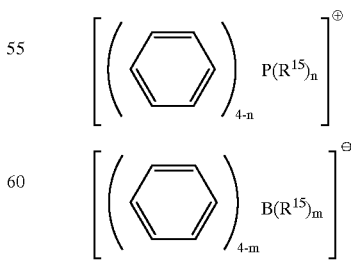

In the formula, n and m are integers of 1 to 4, and $R^{15}$ is represented by the following formula.

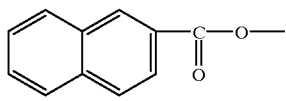

Examples 8–14 and Comparative Examples 1–2

Epoxy resin compositions were prepared by using the epoxy resin, phenolic resin and Reaction Products A to G as shown in Table 1 and 1.5 parts of wax E, 1 part of carbon black, 600 parts of spherical fused silica powder (mean particle size of 20 μm, manufactured by Tatsumori Corporation), and 2 parts of γ-glycidoxypropyTtrimethoxysilane, and uniformly melt mixing them in a hot two-roll mill, followed by cooling and comminution. In Comparative Examples 1 and 2, epoxy resin compositions were similarly prepared using unreacted TPP-K and triphenylphosphine, respectively.

For comparison, the epoxy resin compositions were examined for the following properties. The results are also shown in Table 1.

(1) Spiral Flow

The spiral flow was measured according to EMMI standards by molding the composition in a mold at 175° C. and 70 kgf/cm$^2$.

(2) Hardness When Hot

A rod measuring 100×10×4 mm was molded at 175° C. and 70 kgf/cm$^2$ for 90 seconds. The hardness when hot was measured with a Barcol Impressor.

(3) Shelf Stability

An epoxy resin composition was allowed to stand at 25° C. The days passed until the spiral flow value reduced to 80% of the initial value was counted.

(4) Gel Time

The gel time was measured at 175° C.

(5) Melt Viscosity

The melt viscosity was measured at 175° C. with a constant-load orifice-type flow testing apparatus of the kind known in Japan as a Koka-type flow tester (Shimadzu Mfg. K.K.).

(6) Adhesion

An epoxy resin composition was molded on a copper plate at 175° C. and 70 kgf/cm$^2$ for 2 minutes to form a cylindrical part having a diameter of 15 mm and a height of 5 mm, which was post cured at 180° C. for 4 hours. Using a push-pull gage, a force necessary to separate the molded part from the copper plate was measured.

(7) Peak Temperature on DSC

Using a differential scanning calorimeter, a sample was measured for exothermic peak temperature by heating from 30° C. to 250° C. at a rate of 10.0° C./min. A higher exothermic peak temperature indicates greater potential curing.

TABLE 1

| | | E8 | E9 | E10 | E11 | E12 | E13 | E14 | CE1 | CE2 |
|---|---|---|---|---|---|---|---|---|---|---|
| Composition (parts by weight) | Epoxy resin | 58.4 | 58.4 | 58.4 | 58.4 | 58.4 | 58.4 | 58.4 | 58.4 | 58.4 |
| | Phenolic resin | 41.6 | 41.6 | 41.6 | 41.6 | 41.6 | 41.6 | 41.6 | 41.6 | 41.6 |
| | Reaction Product A | 1.3 | — | — | — | — | — | — | — | — |
| | Reaction Product B | — | 1.4 | — | — | — | — | — | — | — |
| | Reaction Product C | — | — | 2.1 | — | — | — | — | — | — |
| | Reaction Product D | — | — | — | 2.3 | — | — | — | — | — |
| | Reaction Product E | — | — | — | — | 2.8 | — | — | — | — |
| | Reaction Product F | — | — | — | — | — | 1.7 | — | — | — |
| | Reaction Product G | — | — | — | — | — | — | 1.9 | — | — |
| | Triphenylphosphine | — | — | — | — | — | — | — | — | 0.8 |
| | TPP-K | — | — | — | — | — | — | — | 1.2 | — |
| Test results | Spiral flow (inch) | 45 | 42 | 48 | 46 | 45 | 47 | 49 | 64 | 32 |
| | Hardness when hot | 85 | 84 | 86 | 84 | 85 | 82 | 83 | 67 | 91 |
| | Storage stability (day) | 10< | 10< | 10< | 10< | 10< | 10< | 10< | 10< | 3 |
| | Gel time (sec) | 33 | 32 | 35 | 34 | 33 | 36 | 31 | 44 | 22 |
| | Melt viscosity (poise) | 250 | 230 | 240 | 230 | 250 | 250 | 220 | 230 | 410 |
| | Bonding force to Cu (kgf/cm$^2$) | 28 | 26 | 35 | 25 | 26 | 24 | 26 | 15 | 16 |
| | DSC peak temperature (° C.) | 165 | 170 | 164 | 174 | 172 | 163 | 173 | 181 | 134 |

Note
Epoxy resin: epoxidized biphenyl derivatives (softening point 105° C., epoxy equivalent 190, Yuka Shell Epoxy K.K., YX4000H)
Phenolic resin: naphthalene ring-bearing phenolic resin (softening point 108–112° C., phenolic equivalent 140, Nippon Kayaku K.K., Kayahard NH)

It is evident from Table 1 that as compared with epoxy resin compositions using unreacted tetraphenylphosphonium tetraphenylborate, epoxy resin compositions using the reaction products obtained by reacting tetraphenylphosphonium tetraphenylborate with a proton donor experience a less increase of viscosity during milling, are improved in fast-curing, flow and shelf stabilityas well as adhesion and latency.

Japanese Patent Application No. 10-202742 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A phosphonium borate compound of the following general formula (1):

(1)

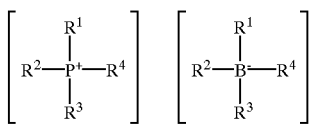

wherein $R^1$, $R^2$, $R^3$ and $R^4$, which may be the same or different, each are a monovalent organic group having an aromatic ring or a monovalent aliphatic group, at least one of $R^1$, $R^2$, $R^3$ and $R^4$ which are bonded to phosphorus atom and at least one of $R^1$, $R^2$, $R^3$ and $R^4$ which are bonded to boron atom are each an organic group derived by releasing a proton from a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule.

2. The phosphonium borate compound of claim 1 having the following general formula (4):

(4)

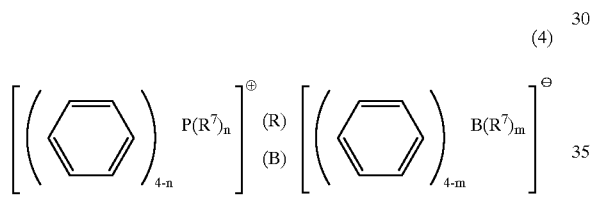

wherein n and m each are an integer of 1 to 4, and $R^7$ is a group selected from groups consisting of the following formulae (5) to (13):

(5)

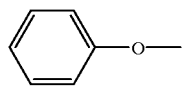

(6)

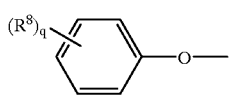

(7)

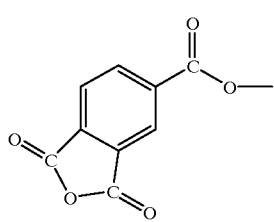

(8)

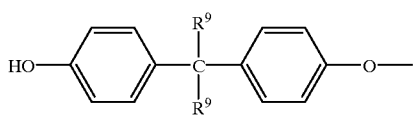

(9)

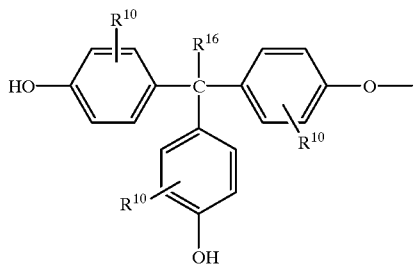

(10)

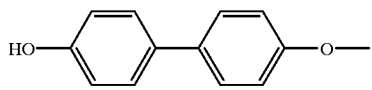

(11)

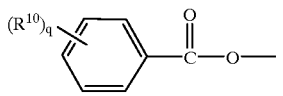

(12)

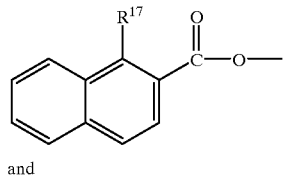

and (13)

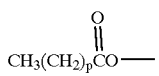

wherein $R^8$ is a halogen atom, alkoxy group or substituted or unsubstituted monovalent hydrocarbon group, $R^9$ is hydrogen, methyl or $CF_3$ group, $R^{10}$ is hydrogen or a substituted or unsubstituted monovalent hydrocarbon group, $R^{16}$ is hydrogen, methyl or ethyl, $R^{17}$ is hydrogen or hydroxyl, p is an integer of 10 to 40, and q is an integer of 1 to 3.

3. A curing catalyst for epoxy resin compositions comprising the phosphonium borate compound of claim 1 or 2.

4. An epoxy resin composition comprising the curing catalyst of claim 3.

5. The phosphonium borate compound of claim 1, having the formula

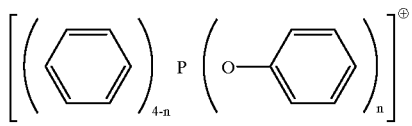

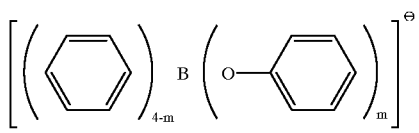

wherein n and m are integers of 1 to 4.

6. The phosphonium borate compound of claim 1, having the formula

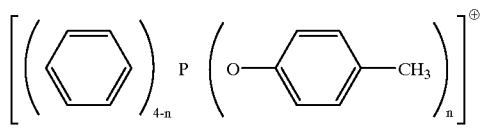

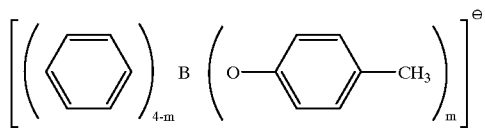

wherein n and m are integers of 1 to 4.

7. The phosphonium borate compound of claim 1, having the formula

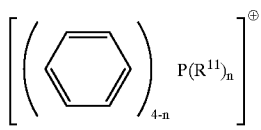

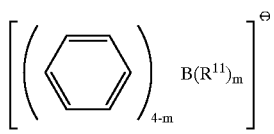

wherein $R^{11}$ is a moiety of the formula

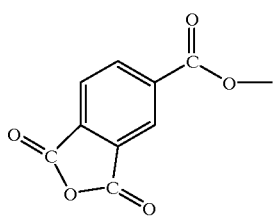

and n and m are integers of 1 to 4.

8. The phosphonium borate compound of claim 1, having the formula

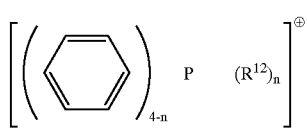

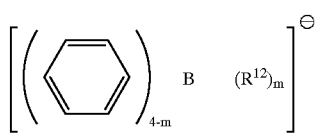

wherein $R^{12}$ is a moiety of the formula

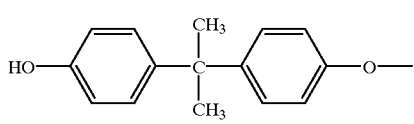

and n and m are integers of 1 to 4.

9. The phosphonium borate compound of claim 1, having the formula

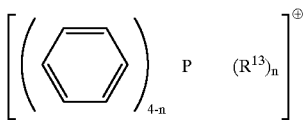

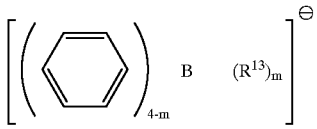

wherein $R^{13}$ is a moiety of the formula

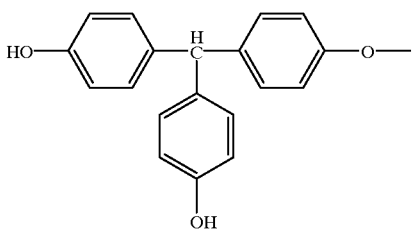

and n and m are integers of 1 to 4.

10. The phosphonium borate compound of claim 1, having the formula

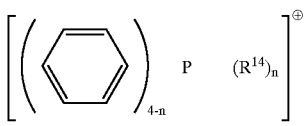

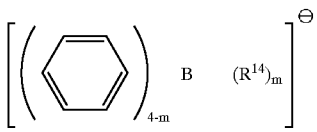

wherein $R^{14}$ is a moiety of the formula

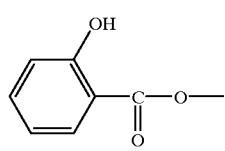

and n and m are integers of 1 to 4.

11. The phosphonium borate compound of claim 1, having the formula

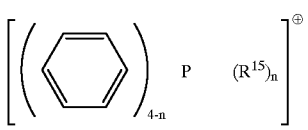

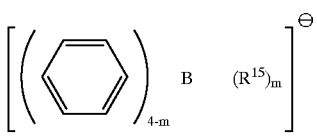

wherein $R^{15}$ is a moiety of the formula

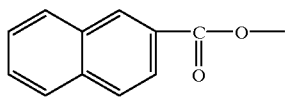

and n and m are integers of 1 to 4.

12. A method for preparing a phosphonium borate compound of the following general formula (1):

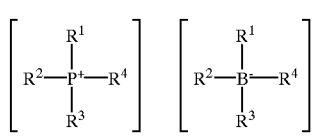
(1)

wherein $R^1$, $R^2$, $R^3$ and $R^4$, which may be the same or different, each are a monovalent organic group having an aromatic ring or a monovalent aliphatic group, at least one of $R^1$, $R^2$, $R^3$ and $R^4$ which are bonded to phosphorus atom and at least one of $R^1$, $R^2$, $R^3$ and $R^4$ which are bonded to boron atom are each an organic group derived by releasing a proton from a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule, said method comprising the step of reacting at a temperature of 120 to 250° C. a phosphonium borate compound of the following general formula (2) with at least one compound of the following general formula (3):

$$[(R^5)_4P]^+[(R^5)_4B]^-$$ (2)

$$HO-(R^6)$$ (3)

wherein $R^5$ is a monovalent organic group having an aromatic ring, and $R^6$ is a monovalent organic group having an aromatic or heterocyclic ring or monovalent aliphatic group, the compound of formula (3) being a proton donor selected from the group consisting of an aromatic carboxylic acid having at least one carboxyl group in a molecule, an aromatic carboxylic acid having at least one acid anhydride group and at least one carboxyl group in a molecule, a phenol compound having at least one phenolic hydroxyl group in a molecule, an aromatic compound having at least one carboxyl group and at least one phenolic hydroxyl group in a molecule, and an aliphatic carboxylic acid having at least one carboxyl group in a molecule.

13. The method of claim 12 wherein the phosphonium borate compound of formula (2) is represented by the following formula (14):

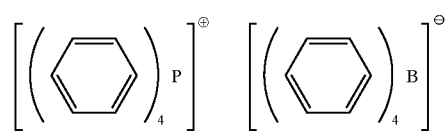
(14)

and the compound of formula (3) is at least one of compounds of the following formulae (15) to (23):

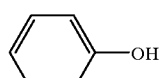
(15)

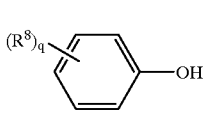
(16)

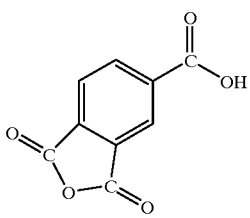
(17)

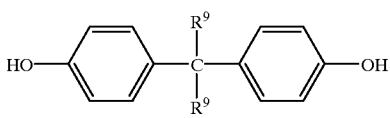
(18)

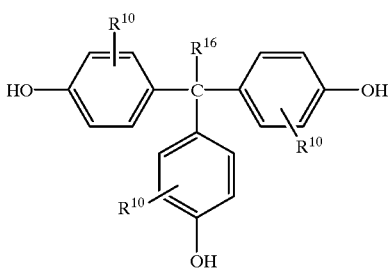
(19)

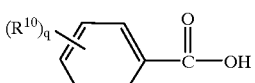
(20)

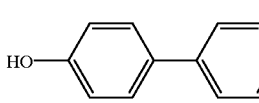
(21)

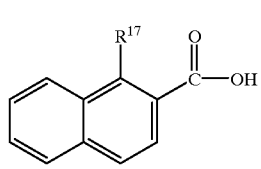
(22)

-continued
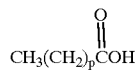
(23)
wherein $R^8$ is a halogen atom, alkoxy group or substituted or unsubstituted monovalent hydrocarbon group, $R^9$ is hydrogen, methyl or $CF_3$ group, $R^{10}$ is hydrogen or a substituted or unsubstituted monovalent hydrocarbon group, $R^{16}$ is hydrogen, methyl or ethyl, $R^{17}$ is hydrogen or hydroxyl, p is an integer of 10 to 40, and q is an integer of 1 to 3.
* * * * *